(12) United States Patent
McCauley

(10) Patent No.: US 8,141,411 B2
(45) Date of Patent: Mar. 27, 2012

(54) METHOD FOR DETERMINING A LOW CYLINDER PRESSURE CONDITION FOR A GAS CHROMATOGRAPH

(75) Inventor: Edward B. McCauley, Cedar Park, TX (US)

(73) Assignee: Thermo Finnigan LLC, San Jose, CA (US)

( * ) Notice: Subject to any disclaimer, the term of this patent is extended or adjusted under 35 U.S.C. 154(b) by 650 days.

(21) Appl. No.: 12/241,518

(22) Filed: Sep. 30, 2008

(65) Prior Publication Data

US 2010/0077838 A1    Apr. 1, 2010

(51) Int. Cl.
*G01N 30/02* (2006.01)
*B01D 53/30* (2006.01)

(52) U.S. Cl. .............. 73/23.42; 95/12; 95/19; 95/22; 95/23

(58) Field of Classification Search .......... 73/23.41, 73/23.42; 95/12, 19, 22, 23
See application file for complete search history.

(56) References Cited

U.S. PATENT DOCUMENTS

| | | | |
|---|---|---|---|
| 4,123,236 A * | 10/1978 | Hirschfeld et al. | ............. 96/104 |
| 4,760,732 A | 8/1988 | Bredeweg et al. | |
| 4,872,334 A * | 10/1989 | Watanabe | ............ 73/23.24 |
| 4,962,042 A * | 10/1990 | Morabito et al. | ............ 436/161 |
| 4,994,096 A | 2/1991 | Klein et al. | |
| 5,163,979 A | 11/1992 | Patrick et al. | |
| 5,339,673 A | 8/1994 | Nakagawa et al. | |
| 5,431,712 A | 7/1995 | Henderson et al. | |
| 5,467,635 A * | 11/1995 | Nakagawa et al. | .......... 73/23.35 |
| 5,476,000 A | 12/1995 | Henderson et al. | |
| 5,496,733 A * | 3/1996 | Spandau et al. | ............... 436/52 |
| 5,524,084 A | 6/1996 | Wang et al. | |
| 5,542,286 A | 8/1996 | Wang et al. | |
| 5,545,252 A | 8/1996 | Hinshaw et al. | |
| 5,567,227 A | 10/1996 | Henderson | |
| 5,803,951 A | 9/1998 | Wada et al. | |
| 5,915,269 A | 6/1999 | Cahill et al. | |
| 5,938,817 A | 8/1999 | Shibamoto et al. | |
| 5,952,556 A | 9/1999 | Shoji | |
| 6,338,823 B1 | 1/2002 | Furukawa | |
| 6,494,078 B1 | 12/2002 | Klee | |
| 7,258,132 B2 | 8/2007 | Henderson et al. | |
| 2003/0126908 A1 | 7/2003 | Furukawa | |
| 2004/0238040 A1 | 12/2004 | Furukawa | |

* cited by examiner

*Primary Examiner* — Daniel Larkin
(74) *Attorney, Agent, or Firm* — Charles B. Katz; Pamela Lau Kee

(57) ABSTRACT

A method for determining a low cylinder pressure condition of a gas chromatograph includes providing gas from the cylinder to an inlet of the gas chromatograph. In particular, the gas is provided at a predetermined inlet pressure that is higher than an inlet pressure that is required for a predetermined gas chromatographic analysis routine. The inlet pressure of the gas being supplied to the inlet is increased, in order to attempt to achieve a predetermined check value. It is then determined if the inlet pressure actually increases to at least the predetermined check value. If it is determined that the inlet pressure of the gas does not increase to at least the predetermined check value, then an indication of a low cylinder pressure condition is provided.

12 Claims, 4 Drawing Sheets

METHOD FOR DETERMINING A LOW CYLINDER PRESSURE CONDITION FOR A GAS CHROMATOGRAPH

FIELD OF THE INVENTION

The instant invention relates generally to gas chromatography, and more particularly to a method for determining a low cylinder pressure condition for a gas chromatograph.

BACKGROUND OF THE INVENTION

Gas chromatography is essentially a physical method of separation in which constituents of a test sample in a carrier gas are adsorbed and desorbed by a stationary phase material in a column. A pulse of the sample is injected into a steady flow of carrier gas. At the end of the column the individual components are separated in time. Detection of the gas provides a time-scaled pattern, which by calibration or comparison with known samples indicates the constituents of the test sample. The main components of such a system are the column, an injector with a mixing chamber for introducing the sample into the carrier gas, a detector at the outlet end of the column, gas controls and a device such as a computer for treating and displaying the output of the detector. An oven may be used to control the temperature of the column, so as to maintain the sample in a volatile state, and to improve the separation of constituents.

Gas chromatographs (GCs) of the current art typically employ electronic pressure control of the column head pressure in order to optimize chromatographic separations and/or run times. On these devices, a low column pressure condition can be sensed when the pressure sensor feedback indicates that a setpoint condition cannot be achieved. When this occurs, an alarm can be indicated to the operator.

Often times this low pressure condition is caused by a gradual and eventual depletion of the carrier gas cylinder contents. This slow and gradual depletion often causes an operator to check the cylinder pressure only on an occasional basis and can result in neglect, which will ultimately cause a low carrier condition to be sensed. Unfortunately, by the time the GC has sensed the low carrier condition it is too late. The analysis underway has been compromised in that an appropriate pressure for accurate retention times or an appropriate inlet pressure during the injection cycle has not been satisfied. The problem is exacerbated when the instrument is running a sequence of samples, since the entire sequence may need to be re-analyzed.

One solution to this problem is to add an additional pressure sensor upstream of the proportional valve in order to sense a low supply line pressure. The regulator delivering a pressure to the GC could be set to higher pressure than that used for the analysis, and the trigger point for an alarm set to correspond to a pressure slightly under the delivered regulator pressure. This would allow sufficient time for an entire sequence of samples to be finished before the operator needed to change cylinders. Unfortunately this solution to the problem adds cost to the electronic pressure control pneumatics and so is generally not implemented. Furthermore, the need to add an additional pressure sensor to the pneumatic control system creates a barrier to implementing this solution in existing gas chromatographs.

Accordingly, there exists a need for a method that overcomes at least some of the above-mentioned limitations.

SUMMARY OF EMBODIMENTS OF THE INVENTION

According to an aspect of the invention there is provided a method for determining a low cylinder pressure condition of a gas chromatograph, the method comprising: providing gas from the cylinder to an inlet of the gas chromatograph, the gas being provided at a predetermined inlet pressure during a first period of time; during a second period of time, increasing the inlet pressure of the gas that is being provided from the cylinder; determining if the inlet pressure increases to at least a predetermined check value during the second period of time; and, if it is determined that the inlet pressure of the gas does not increase to at least the predetermined check value, providing an indication of a low cylinder pressure condition.

According to an aspect of the invention there is provided a method for determining a low cylinder pressure condition of a gas chromatograph, the method comprising: providing a supply of gas from the cylinder to a component of the gas chromatograph, the supply of gas for supporting operation of the gas chromatograph according to a predetermined analytical method during a first period of time; providing during a second period of time an increased supply of gas from the cylinder to the component of the gas chromatograph, the increased supply of gas for achieving, absent a low cylinder pressure condition, a predetermined check condition of the gas chromatograph; determining if the predetermined check condition of the gas chromatograph is achieved during the second period of time; and, if it is determined that the predetermined check condition of the gas chromatograph is not achieved during the second period of time, providing an indication of a low cylinder pressure condition.

According to an aspect of the invention there is provided a method for determining a low cylinder pressure condition of a gas chromatograph, the method comprising: providing a supply of gas from the cylinder to a component of the gas chromatograph, the supply of gas for supporting operation of the gas chromatograph according to a predetermined analytical method during a first period of time; providing during a second period of time an increased supply of gas from the cylinder to the component of the gas chromatograph, the increased supply of gas for achieving, absent a low cylinder pressure condition, a predetermined check condition of the gas chromatograph; determining if the predetermined check condition of the gas chromatograph is achieved during the second period of time; and, if it is determined that the predetermined check condition of the gas chromatograph is not achieved during the second period of time, providing an indication of a low cylinder pressure condition.

BRIEF DESCRIPTION OF THE DRAWINGS

Exemplary embodiments of the invention will now be described in conjunction with the following drawings, in which similar reference numerals designate similar items.

DETAILED DESCRIPTION OF EMBODIMENTS OF THE INSTANT INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the scope of the invention. Thus, the present invention is not intended to be limited to the embodiments disclosed, but is to be accorded the widest scope consistent with the principles and features disclosed herein.

Figure 1:
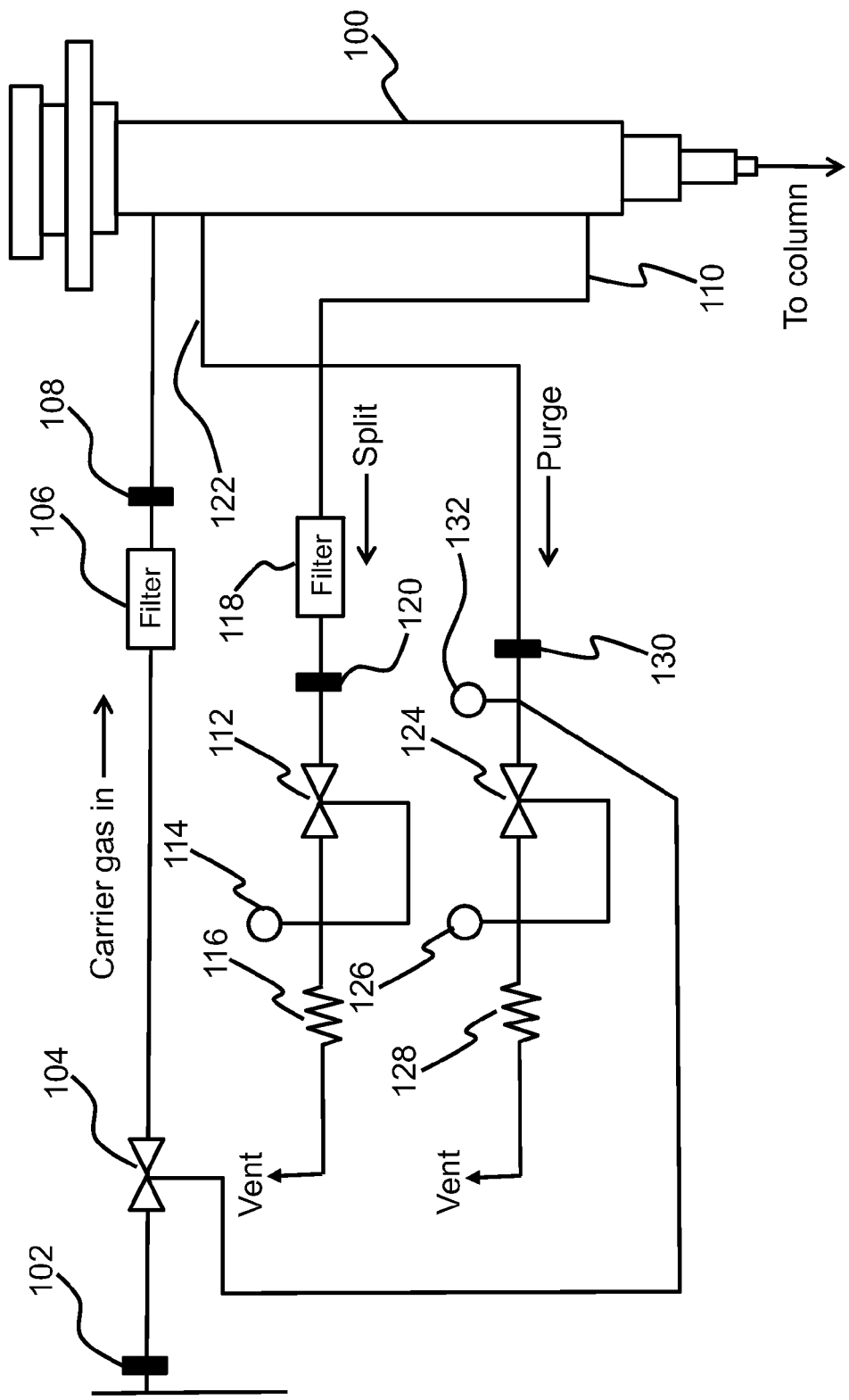
FIG. 1 is a simplified schematic diagram showing a conventional gas chromatograph pneumatic control system suitable for use with a method according to an embodiment of the instant invention.

Referring to FIG. 1, shown is a simplified schematic diagram of a conventional gas chromatograph pneumatic control system that is suitable for use with a method according to an embodiment of the instant invention. In this specific and non-limiting example, a split/splitless type inlet 100 is provided in communication with one end of a chromatographic column (not shown). Regulated carrier gas flow through frit 102 is provided via a flow controller, such as for instance a proportional valve 104, to the inlet 100. The operation of the flow controller serves to adjust and control the pressure and/or the volumetric flow rate of the carrier gas in the GC system. The carrier gas may comprise one or more component gasses such as hydrogen, nitrogen, or helium, depending on the chromatographic separation being performed. Additional elements, such as for instance filter 106 and frit 108, ensure that the carrier gas is sufficiently free of contaminants prior to being provided into the inlet 100.

During operation in the split injection mode, a sample is introduced into the heated inlet 100 where it vaporizes. A small amount of the sample/carrier gas mixture enters the column while the majority of the sample/carrier gas mixture is vented out to the split line 110. The split line flow is maintained constant using proportional valve 112, which receives a feedback signal from a pressure sensor 114 located downstream therefrom. The pressure sensor 114 and proportional valve 112 cooperate to provide a constant gas pressure supplied to the upstream side of restrictor 116, thereby ensuring constant gas flow rate to ambient via the split line vent. Additional elements, such as for instance filter 118 and frit 120, reduce fouling of the downstream components of the split line 110. By way of a specific and non-limiting example, a suitable split line flow rate is approximately 50 cc/min.

As the carrier gas containing the sample exits the not illustrated column, the presence of one or more sample constituent components is detected using a not illustrated detector. The detector optionally is any one of the GC detectors known in the art, so long as it is capable of determining at least one physiochemical property of the carrier fluid that exits column. The term "detector" includes a wide variety of useful chromatographic detectors, such as flame ionization detectors, photoionization detectors, nitrogen phosphorous detectors, flame photometric detectors, thermal conductivity detectors, atomic emission detectors, electrolytic conductivity detectors, and electron capture detectors. Mass spectral detectors and infrared spectral detectors are also known.

In addition, some of the carrier gas that is introduced into inlet 100 is used to sweep the inward facing surface of a not illustrated septum thereof. This so-called septum purge flow prevents air diffusion into the column and minimizes the appearance of false peaks resulting from desorption, from the surface of the septum, of previously injected samples. The septum purge flow passes from the inlet 100 to purge line 122. The purge line flow is maintained constant using proportional valve 124, which receives a feedback signal from a pressure sensor 126 located downstream therefrom. The pressure sensor 126 and proportional valve 124 cooperate to provide a constant gas pressure supplied to the upstream side of restrictor 128, thereby ensuring constant gas flow rate to ambient via the purge line vent. Additional elements, such as for instance frit 130, reduce fouling of the downstream components of the purge line 122. By way of a specific and non-limiting example, a suitable purge line flow rate is approximately 5 cc/min.

A pressure sensor 132 is also disposed along purge line 122 between frit 130 and proportional valve 124. The pressure sensor 132 provides a control voltage for controlling proportional valve 104, so as to thereby maintain the inlet pressure at a predetermined setpoint value. In this way, the pressure sensor 132 measures the inlet pressure and provides feedback control to the proportional valve 104. For a particular flow rate through the proportional valve 104, the measured inlet pressure depends on the column length and diameter, as well as the temperature of the column. Increasing the flow rate through proportional valve 104 results in increased inlet pressure, while decreasing the flow rate through proportional valve 104 results in decreased inlet pressure.

Pressure sensor 132 and proportional valve 104, as well as other components of the pneumatic control system, communicate with and operate under the control of a data and control system (not depicted), which may take the form of any one or a combination of general-purpose and/or specialized processors and application-specific circuitry. The data and control system will typically be configured to execute software instructions encoding the methods described hereinbelow.

In a conventional gas chromatograph pneumatic control system, such as for instance the one that is described with reference to FIG. 1, an alarm may be indicated to the operator when the inlet pressure as measured by pressure sensor 132 falls below a predetermined setpoint value. Unfortunately, the alarm sounds too late if a series of analyses has already begun. Under this condition, the entire series of analyses may need to be repeated. An alternate solution, as was discussed above, is to provide an additional pressure sensor along the carrier gas inlet route, such as for instance between the carrier gas source and proportional valve 104, in order to provide earlier warning of a low carrier pressure condition.

Figure 2:
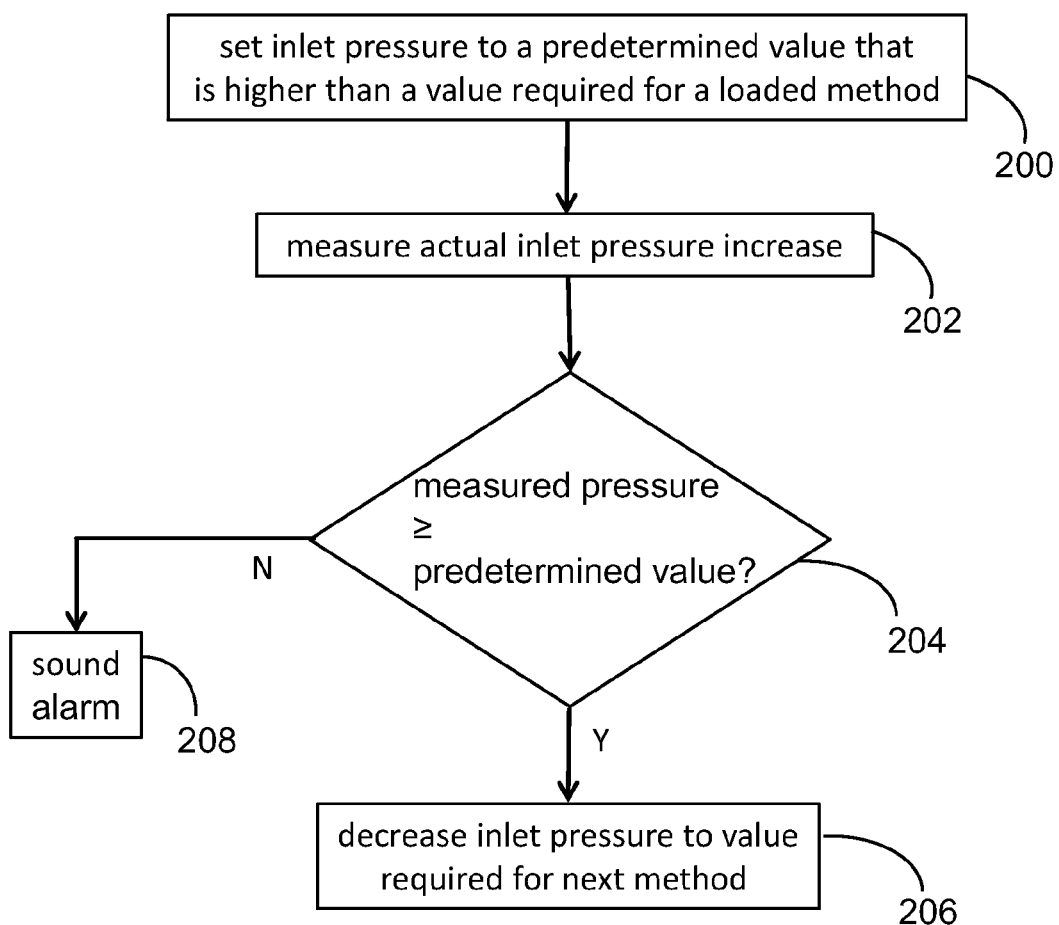
FIG. 2 is a simplified flow diagram showing a method according to an embodiment of the instant invention.
Figure 3:
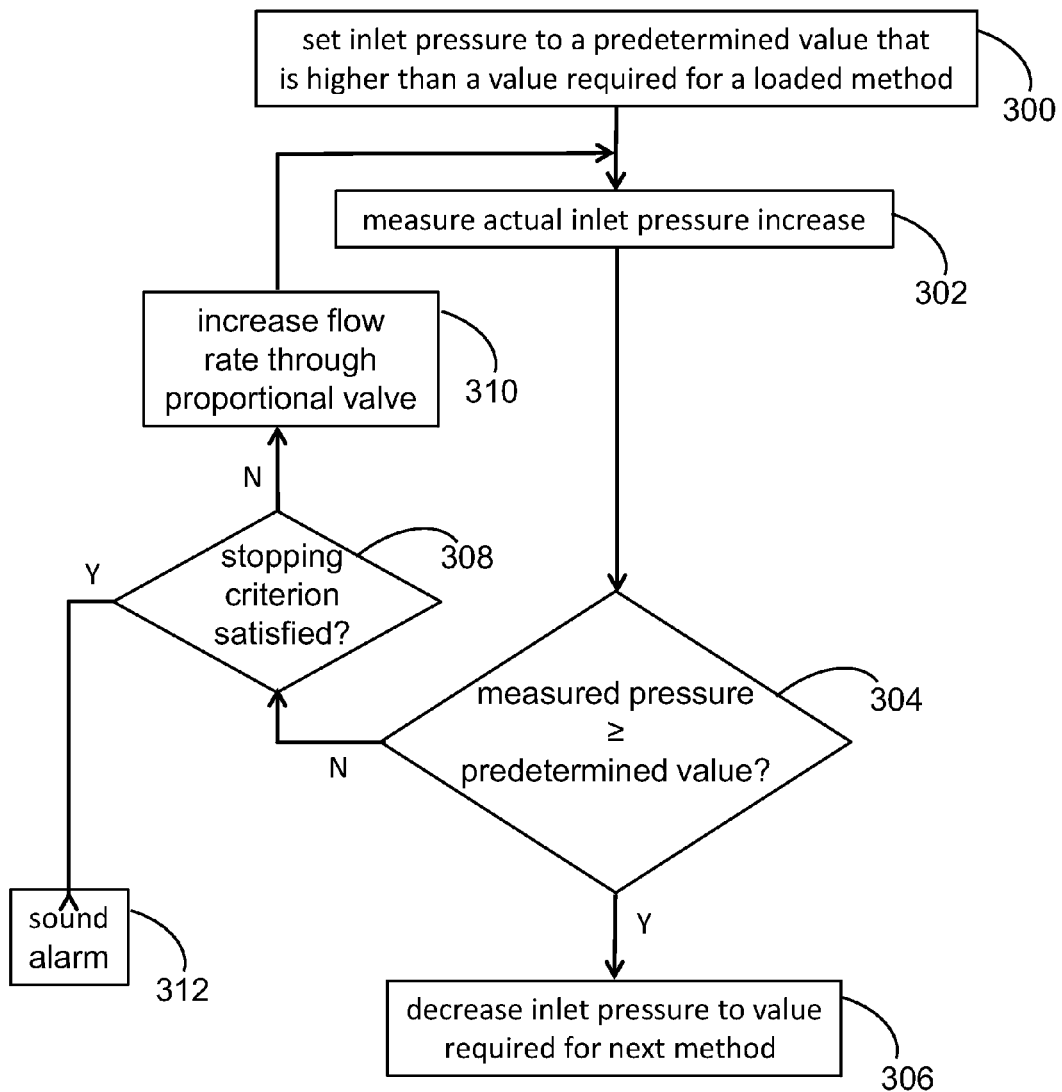
FIG. 3 is a simplified flow diagram showing a method according to an embodiment of the instant invention; and, FIG. 4 is a simplified flow diagram showing a method according to an embodiment of the instant invention.

Referring now to FIGS. 2 and 3, shown are simplified flow diagrams of methods for detecting a low carrier pressure condition of a gas chromatograph, according to embodiments of the instant invention. The methods that are shown in FIGS. 2 and 3 each use conventional electronic control pneumatics of current design, such as that described with reference to FIG. 1, to check the carrier gas supply line pressure. Advantageously, the methods as shown in FIGS. 2 and 3 are implementable in existing gas chromatograph systems. It is also envisaged that the methods as shown in FIGS. 2 and 3 will be implementable in similar gas chromatograph systems that may be developed in the future. For instance, the method may be encoded in a software module that is provided as part of a firmware upgrade or as part of a software update/upgrade. Of course, new gas chromatograph systems preferably are shipped to the end user with the necessary software for performing the method according to at least one of FIGS. 2 and 3. Ideally, the backpressure exerted by the protective frit 130 is minimal so as to reduce the pressure error of sensor 132 during large purge flows.

The methods according to FIGS. 2 and 3 are performed typically in an automated fashion according to scheduling criteria that are provided, for example, by one of the user of the gas chromatograph and the supplier/manufacturer of the gas chromatograph. For instance, the method according to FIG. 2 or 3 is executed following a gas chromatographic run, or immediately preceding one, or is part of an established gas chromatographic analysis routine. Optionally, the scheduling is a clock-time event or a run-time event. The methods according to FIGS. 2 and 3 may be executed in real time at regular intervals, for instance at a same time each day during off-peak or off-work hours. Alternatively, the methods according to FIGS. 2 and 3 may be executed on a daily or weekly basis, or on another suitable scheduling basis, but at a time that does not interfere with a chromatographic analysis that is already in progress. Optionally, a user may initiate the method of FIG. 2 or 3 at any other convenient time in a manual fashion. For instance, the user interface of the gas chromatography system provides the user with an option for initiating the method according to at least one of FIGS. 2 and 3 upon demand. This allows a user to check the gas supply prior to beginning an unusually long series of analyses, prior to leaving an analysis to run unsupervised for a prolonged period of time, or simply at any other time that the user anticipates the gas supply may be nearly exhausted.

Referring now to FIG. 2, shown is a simplified flow diagram of a method according to an embodiment of the instant invention. The method begins at 200 by setting the inlet pressure to a predetermined check value that is higher than what is required for a predetermined gas chromatographic analysis routine. For instance, a control voltage is provided from pressure sensor 132 to proportional valve 104 to increase the carrier gas flow rate therethrough, so as to thereby attempt to adjust the inlet pressure to the predetermined check value. In particular, the predetermined check value is lower than the regulator pressure of the carrier gas source. By way of a specific and non-limiting example, the carrier gas source pressure (i.e. cylinder pressure) in a typical system is approximately 2000 p.s.i., the regulator pressure is approximately 150 p.s.i., and the inlet pressure required for the loaded method is approximately 10-20 p.s.i. Under such typical conditions, a suitable predetermined value for the inlet pressure is approximately 90 p.s.i. In general, the predetermined check value is between about two and four times the inlet pressure that is required for the predetermined gas chromatographic analysis routine, and additionally is at least about 50% of a regulator pressure setting of the cylinder.

Next, at 202, the actual inlet pressure increase that is achieved is measured using pressure sensor 132. If it is determined at 204 that the actual inlet pressure has increased to the predetermined check value, then at 206 the inlet pressure is decreased to a value that is required for the predetermined gas chromatographic analysis routine, or to a value that is required for a next routine to be loaded, and the gas chromatograph system is ready to perform the next series of analyses. If it is determined at 204 that the actual inlet pressure did not increase to the predetermined check value then at 208 an alarm is sounded to the user to warn of a low carrier supply condition. Optionally, the inlet pressure is still decreased to a value that is suitable for operation of the gas chromatograph according to the predetermined gas chromatographic analysis routine, since even when the alarm is sounded the volumetric capacity of the gas cylinder ensures a period of continued operation of the gas chromatograph. The user may then, for instance, complete additional analyses prior to taking the time to change the gas cylinder.

Referring now to FIG. 3, shown is a simplified flow diagram of a method according to an embodiment of the instant invention. The method begins at 300 by setting the inlet pressure to a predetermined check value that is higher than what is required for a predetermined gas chromatographic analysis routine. For instance, a control voltage is provided from pressure sensor 132 to proportional valve 104 to increase the carrier gas flow rate therethrough, so as to thereby attempt to adjust the inlet pressure to the predetermined check value. In particular, the predetermined check value is lower than the regulator pressure of the carrier gas source. By way of a specific and non-limiting example, the carrier gas source pressure (i.e. cylinder pressure) in a typical system is approximately 2000 p.s.i., the regulator pressure is approximately 150 p.s.i., and the inlet pressure required for the loaded method is approximately 10-20 p.s.i. Under such typical conditions, a suitable predetermined value for the inlet pressure is approximately 90 p.s.i. In general, the predetermined check value is between about two and four times the inlet pressure that is required for the predetermined gas chromatographic analysis routine, and additionally is at least about 50% of a regulator pressure setting of the cylinder.

Next, at 302, the actual inlet pressure increase is measured using pressure sensor 132. If it is determined at 304 that the actual inlet pressure has increased to the predetermined check value, then at 306 the inlet pressure is decreased to a value that is required for the predetermined gas chromatographic analysis routine, or to a value that is required for a next routine that is to be loaded, and the gas chromatograph system is ready to perform a next series of analyses. If it is determined at 304 that the actual inlet pressure did not increase to the predetermined check value, and if a stopping criterion has not been satisfied at 308, then at 310 the pressure sensor provides a control voltage to the proportional valve to further increase the carrier gas flow rate therethrough. The method continues until the measured inlet pressure increases to the predetermined check value, or until the stopping criterion is satisfied at 308, such as for instance when the measured inlet pressure is, during a predetermined number of iterations, approximately constant and lower than the predetermined check value. When the stopping criterion is satisfied at 308, then at 312 an alarm is indicated to the user to warn of a low carrier supply condition. Optionally, the inlet pressure is still decreased to a value that is suitable for operation of the gas chromatograph according to the predetermined gas chromatographic analysis routine, since even when the alarm is sounded the volumetric capacity of the gas cylinder ensures a period of continued operation of the gas chromatograph. The user may then, for instance, complete additional analyses prior to taking the time to change the gas cylinder.

Preferably, enabling of the methods for checking the carrier cylinder pressure is user selectable in order to prevent an undesirable instrument effect, such as for instance a flame out condition of an FID or an excessive pressure in the manifold of a mass spectrometer. Similarly, it is also preferable that the predetermined check value is user selectable.

Optionally, the methods that are described with reference to FIG. 2 or 3 are used to determine a low cylinder pressure condition for a gas other than that supplied to the inlet. For instance, the methods according to the instant invention may be used to detect low supply condition of gases that are supplied to conventional gas chromatographic detector pneumatic modules, such as argon/methane, hydrogen, air, nitrogen, oxygen, etc.

Figure 4:
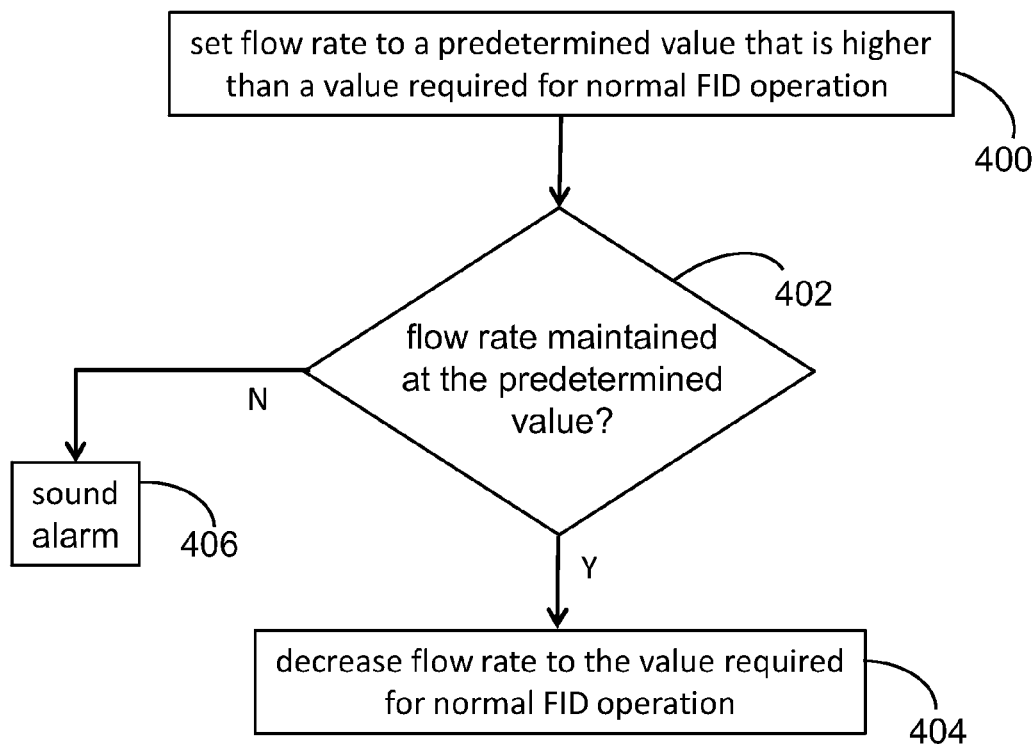

By way of a specific and non-limiting example, the method of FIG. 2 or 3 is readily adapted to detect a low-pressure condition of gases supplied to a flame ionization detector (FID). In a typical system, the FID gas supply line includes a restrictor, a proportional valve and a pressure sensor. Referring now to FIG. 4, the adapted method begins at 400 by setting the gas flow rate through the proportional valve of the FID gas supply line to a predetermined value that is higher than what is needed for normal FID operation. At 402 it is determined if the flow rate through the proportional valve is maintained at the predetermined value. If it is determined that the flow rate through the proportional valve of the FID gas supply line is maintained at the predetermined value, then the flow rate is reduced at 404 to the value that is required for normal FID operation. If it is determined that the flow rate through the proportional valve of the FID gas supply line is not maintained at the predetermined value, then an alarm is sounded to the user at 406.

Of course, the GC pneumatic control system that is shown in FIG. 1 is merely a specific and non-limiting example of a conventional GC pneumatic control system, which is considered to be suitable for use with the methods that are described above. One of ordinary skill in the art will readily envisage various modifications to the GC pneumatic control system of FIG. 1. Such modified GC pneumatic control systems are also suitable for use with the methods that are described above, provided that a suitable inlet pressure controller and a suitable inlet pressure sensor are present. Of course, the software that is provided with the GC system may need to be adapted in dependence upon the specific pneumatic control system thereof.

In the methods that are described with reference to FIGS. 2 through 4, it is to be understood that the alarm is any human intelligible indication for indicating the detected low gas supply condition. Thus, audible alarms as well as optically recognizable alarms are envisaged. The alarms may comprise a text alert, an e-mail or another similar message being sent to the user either via the user interface of the gas chromatograph system, or via a wireless communication channel or the internet. Thus, it is envisaged that the user may be notified of the low gas supply condition when at a location that is remote from the gas chromatograph system.

Numerous other embodiments may be envisaged without departing from the scope of the instant invention.

What is claimed is:

1. A method for determining a low cylinder pressure condition of a gas chromatograph, the method comprising:
    providing gas from a cylinder to an inlet of the gas chromatograph, the gas being provided at a predetermined inlet pressure during a first period of time;
    during a second period of time, increasing the inlet pressure of the gas that is being provided from the cylinder;
    determining if the inlet pressure increases to at least a predetermined check value during the second period of time; and,
    if it is determined that the inlet pressure of the gas does not increase to at least the predetermined check value, providing an indication of a low cylinder pressure condition.

2. A method according to claim 1, wherein providing the indication of a low cylinder pressure condition comprises providing a human intelligible alarm.

3. A method according to claim 1, wherein determining if the inlet pressure of the gas increases to at least the predetermined check value comprises sensing an actual inlet pressure of the gas during the second period of time and comparing the sensed inlet pressure of the gas to the predetermined check value.

4. A method according to claim 1, wherein the predetermined inlet pressure of the gas during the first period of time is a first inlet pressure for supporting operation of the gas chromatograph according to a predetermined gas chromatographic analysis routine.

5. A method according to claim 4, comprising decreasing the inlet pressure of the gas to approximately the first inlet pressure during a third period of time that is subsequent to the second period of time.

6. A method according to claim 1, wherein the second period of time is not during the performance of a gas chromatographic analysis routine.

7. A method according to claim 1, wherein the second period of time is during the performance of a gas chromatographic analysis routine.

8. A method according to claim 1, wherein the predetermined check value is between two and four times the predetermined inlet pressure.

9. A method according to claim 1, wherein the predetermined check value is at least 50% of a regulator pressure setting of the cylinder.

10. A method according to claim 1, wherein the second time is scheduled as a clock-time event.

11. A method according to claim 1, wherein the second time is scheduled as a run-time event.

12. A method according to claim 1, wherein increasing the inlet pressure of the gas is performed in an incremental fashion, and wherein determining if the inlet pressure increases to at least the predetermined check value is performed subsequent to each incremental pressure increase.

* * * * *